United States Patent [19]

Evans et al.

[11] 4,189,335

[45] Feb. 19, 1980

[54] METHOD FOR DETERMINING DISTRIBUTION OF A COATING COMPOSITION ON A CARPET STRUCTURE

[75] Inventors: John C. Evans, Midland; Edwin L. Wittbrodt, Auburn, both of Mich.

[73] Assignee: The Dow Chemical Company, Midland, Mich.

[21] Appl. No.: 946,908

[22] Filed: Sep. 28, 1978

[51] Int. Cl.[2] ...................... A47G 27/02; G01B 15/02
[52] U.S. Cl. .......................................... 156/64; 427/10
[58] Field of Search ........................... 427/10; 156/64

[56] References Cited

U.S. PATENT DOCUMENTS

| 2,868,062 | 1/1959 | Haley | 83/14 |
| 3,474,254 | 10/1969 | Piepenbrink et al. | 250/219 |
| 4,029,420 | 6/1977 | Simms | 356/209 |

Primary Examiner—James R. Hoffman

[57] ABSTRACT

The distribution of a coating composition, e.g., a binder composition, on a carpet structure is determined by illuminating the coated carpet surface with light and measuring the intensity of the light returned therefrom. The intensity of the returned light relates to the distribution, i.e., (1) the amount of the illuminated surface which is coated and (2) the depth of said coating, of the coating on the carpet structure.

14 Claims, 3 Drawing Figures

METHOD FOR DETERMINING DISTRIBUTION OF A COATING COMPOSITION ON A CARPET STRUCTURE

BACKGROUND OF THE INVENTION

This invention relates to a method for determining the distribution of a coating composition on a carpet structure.

In the production of carpets such as carpets of the tufted type wherein a plurality of loops of yarn are deposited in a primary backing material, the back surface is generally coated with a binder composition, e.g., a natural or synthetic latex composition or like material. This binder composition imparts to the carpet structure desired physical properties such as anchorage of the carpet yarns and dimensional stability.

In a typical operation, the application of such binder generally comprises transferring the liquid binder composition from an applicator roll which rotates in a bath of said composition to the back side of a carpet structure passing across the top of said rolls. The carpet backing is then exposed to a scraper blade and, optionally, a lick roll, which removes any excess composition which may have been applied. A secondary backing, generally referred to as secondary jute, is then married to the coated carpet and the carpet passed through an oven to dry and/or cure the binder.

In the application process, the quantity of binder applied to the carpet is advantageously that minimum amount required to impart the desired properties to the carpet following the curing and/or drying thereof. To achieve the maximum benefits from such amounts of binder, it is desirable to control its distribution. For example, it is often advantageous to distribute the binder such that prior to the marriage with the secondary jute the primary backing material and carpet yarns exposed on the backing, e.g., loops or tufts, are substantially covered and there is essentially no penetration of the binder to the carpet facing. See, for example, *The Application of Synthetic Resin Emulsions* by H. Warson, published in 1972 by Ernest Benn Limited, London, Chapter X, "Miscellaneous Textile Applications."

Unfortunately, small variations in the application process, e.g., viscosity of the liquid binder composition and pressures exerted by the scraper blade or lick roll, will often cause significant fluctuations in the distribution of the binder on the carpet. Thus, in a normal application process, although identical amounts of binder are applied, the distribution of the binder may vary significantly. Often, due to this variation in distribution, the properties and performance of the resulting carpet are non-uniform.

Heretofore, the distribution of the binder on the back side of the carpet structure has been determined by visual inspection. Unfortunately, such method is inherently inaccurate, not uniformly reproducible, and requires extensive amounts of time. As such, process changes cannot readily be made to correct undesirable distributions of the coating.

In view of the stated deficiencies of the conventional methods for determining the distribution of the coating composition on a carpet structure, it would be highly desirable to provide a method for efficiently determining said distribution.

SUMMARY OF THE INVENTION

Accordingly, the present invention is such a method for readily determining the distribution of a coating composition on a carpet structure, wherein the coating composition and carpet structure being coated have sufficiently different light deflecting properties. In such method, a surface of the carpet structure, at least a portion of which surface has the coating composition thereon, is illuminated by a beam of light. The intensity of a fraction of the light returned therefrom is measured; the intensity of said light fraction varying with the distribution of the coating composition, i.e., the amount of the surface area which is coated and the depth of said coating, on the carpet structure.

By this method, a reproducible and relatively accurate determination of the distribution of a coating composition on a carpet structure is obtained. Moreover, the physical properties of the coated carpet are often calculable from said determination.

As such, the method of this invention is useful for determining the distribution of a backsizing or similar type composition on a carpet structure and for predicting the physical properties of a carpet in both a continuous or batchwise, e.g., laboratory experimental type, operations.

BRIEF DESCRIPTION OF THE DRAWINGS

Understanding of this invention will be facilitated by referring to the accompanying drawings, in which.

DETAILED DESCRIPTION OF PREFERRED EMBODIMENTS

Figure 1:
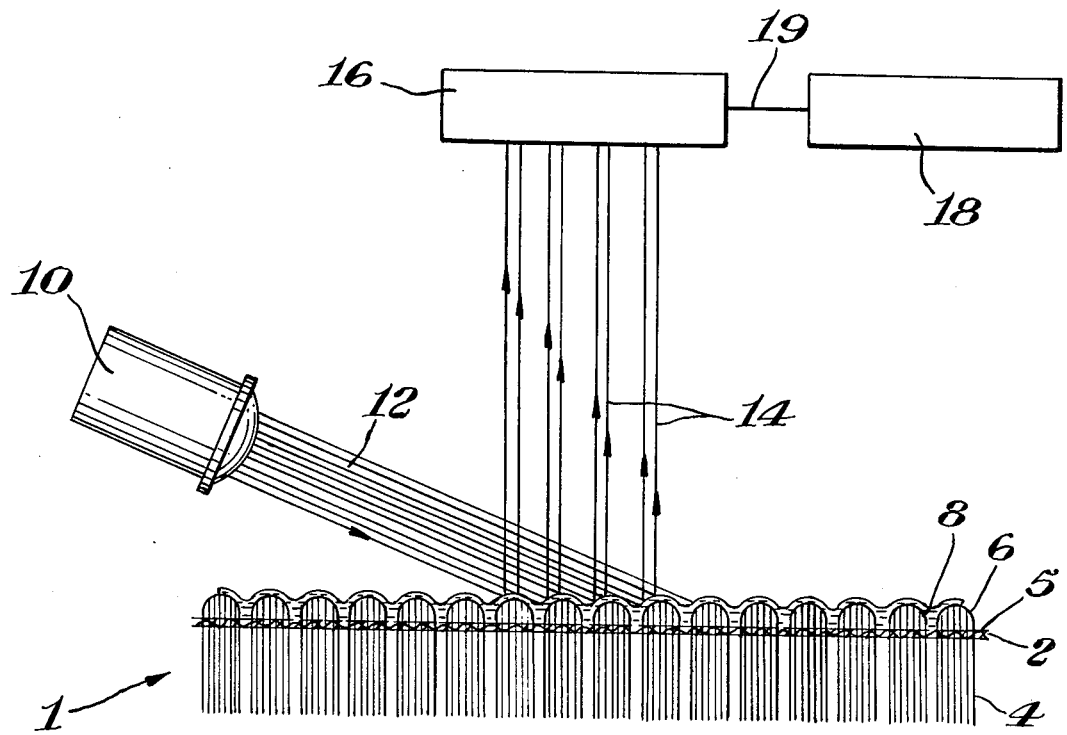
FIG. 1 is a schematic representation which illustrates an embodiment of this invention.
Figure 2:
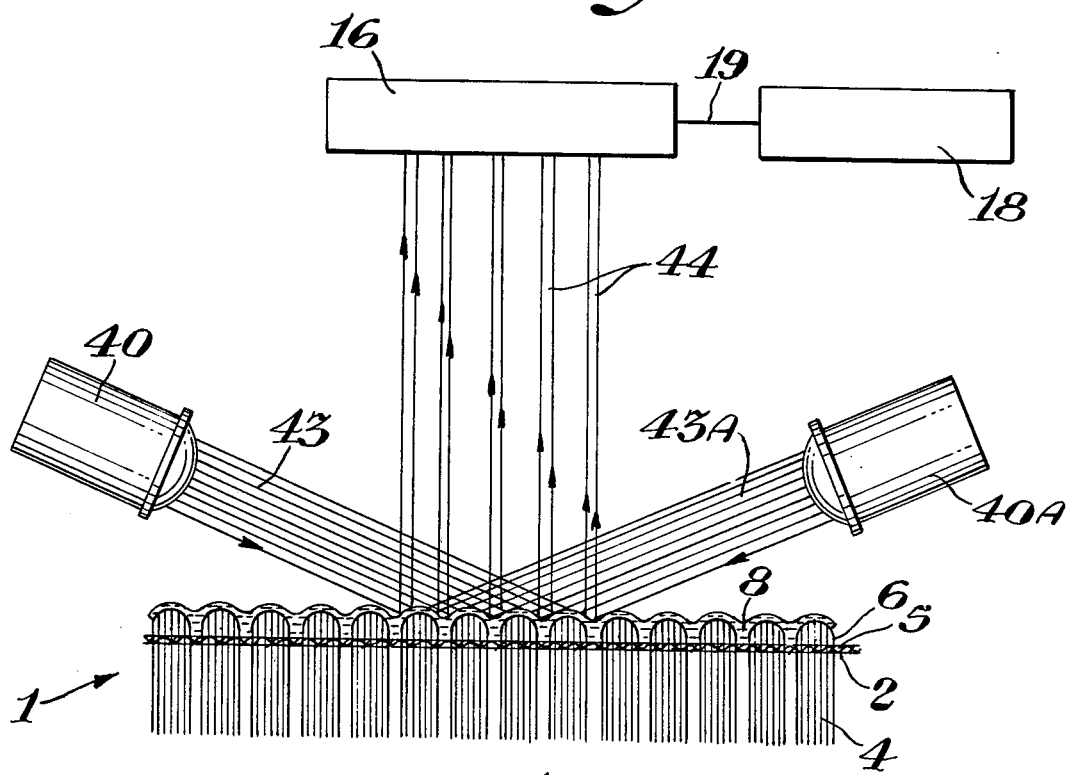
FIG. 2 is a schematic representation which illustrates an alternate embodiment of this invention.

Referring now more particularly to the drawings, FIGS. 1 and 2, which represent embodiments of this invention, depict a tufted carpet section 1, comprising a primary backing material 2 and carpet yarns 4, i.e., fiber bundles, which extend through to the underside 5 of backing material 2 to form loops 6. Deposited on portions of the back surface of the carpet structure, i.e., loops 6 and underside 5 of backing material 2, is a coating composition 8. Coating composition 8 has sufficiently different light deflecting properties than the surface of carpet section 1, being coated, i.e., loops 6 and backing material 2.

In FIG. 1, a light source 10 is positioned at an oblique angle to carpet section 1. A beam of light 12, preferably a beam of collimated light emitted from the light source 10 strikes an area of the tufted carpet section 1. Within this area, the light 12 illuminates portions of the coating composition 8 on backing material 2 and one side of loops 6 and uncoated portions of backing material 2 and one side of loops 6. At least a fraction of the light 14 returned from these illuminated surfaces, i.e., the illuminated surfaces of the coating composition 8 and illuminated uncoated surfaces of loops 6 and backing material 2, falls upon, i.e., strikes, a light detector 16. The intensity of said fraction of light varies with the distribution of coating 8 on carpet section 1. Light detector 16 provides a measurable signal, e.g., an electrical current, which varies with the intensity of this light fraction. This signal is transmitted by lead 19 to recorder means 18 which registers the signal.

In the embodiment illustrated in FIG. 1, the returned light which strikes the detector is primarily composed of that light reflected and/or scattered by the coating 8, loops 6 and backing material 2. Due to the sufficiently different light deflecting properties of the coating 8, loops 6 and backing material 2 (the loops 6 and backing material 2 generally being significantly less reflective than coating 8 and exhibiting only minimal scattering), the intensity of the returned light relates to (1) that amount of the illuminated surface area which has been covered with the coating and/or (2) the depth of said coating. As such, analysis of the signal provided by the detector 16 determines the distribution of the coating on the carpet structure, i.e., that amount of the surface area which has been coated and/or the depth of such coating.

Although one light source is generally employed, for greater accuracy and a truer representation of the distribution of said coating, two or more light sources are often more advantageously employed. FIG. 2 depicts an embodiment of this invention wherein two light sources 40 and 40A are positioned diametrically opposite one another and at an oblique angle to carpet section 1. Advantageously, the angle of incidence, i.e., that angle between the radiation axis of the light source and the backing material of each light source, is about the same. Beams of light 43 and 43A emitted from light sources 40 and 40A, respectively, strike an area of carpet section 1. Within this area, light 43 and 43A illuminates portions of coating composition 8 on backing material 2 and two sides of loops 6 and uncoated portions of backing material 2 and two sides of loops 6. At least a fraction of the light 44 returned from those illuminated portions (the intensity of which fraction varying with the distribution of the coating composition on the carpet section) strikes light detector 16. Light detector 16 converts the intensity of this light fraction into a measurable signal which is transmitted to recorder 18 by lead 19. Analysis of this measurable signal provided by detector 16 determines the distribution of coating composition 8 on carpet section 1.

In a similar manner, three or more light sources are often advantageously employed. Preferably, with such arrangement, the light sources are positioned such that each light source is at approximately the same angle of incidence and the desired surface area of the carpet structure is illuminated. Typically, with light sources having the same angle of incidence, each light source is advantageously essentially equidistant from both light sources adjacent thereto, i.e., the light sources are generally radially symmetric. The number of light sources most advantageously employed in the practice of this invention will vary depending on a variety of factors including the type of carpet structure and the accuracy desired. Such number is easily determined by experimentation.

Figure 3:
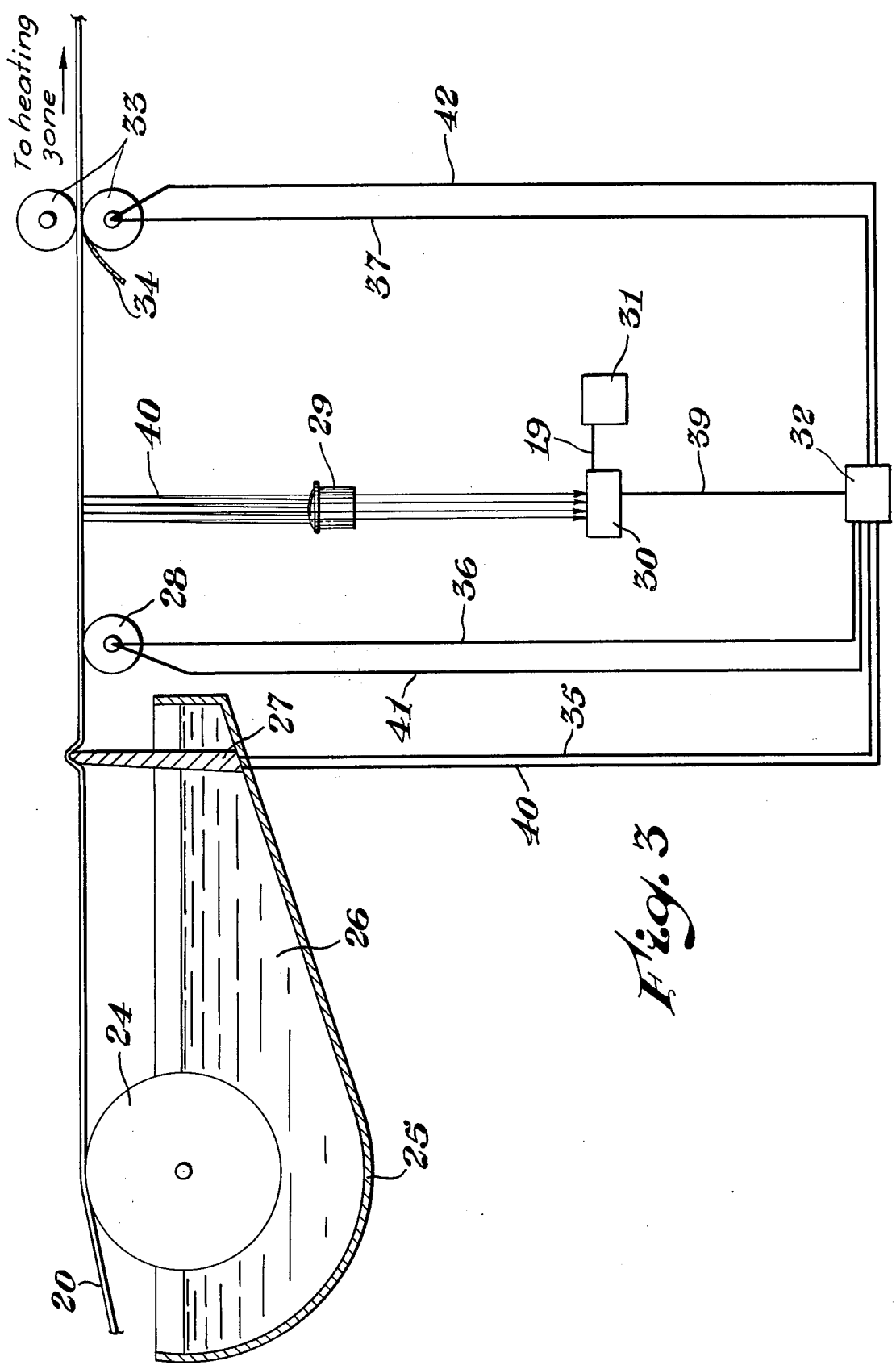
FIG. 3 is a schematic representation illustrating a typical application process for applying a coating composition to a carpet wherein the method of this invention is employed for determining the distribution of said coating on the carpet backing.

FIG. 3 depicts a typical application process, which incorporates the method of this invention, useful in applying a coating composition to a carpet structure, wherein said coating and carpet have sufficiently different light deflecting properties. In said application process, an excess amount of coating composition 26 is applied to carpet structure 20 by passing carpet structure 20 over applicator roll 24 which rotates in a reservoir 25 containing the liquid coating composition 26. This excess amount of composition 26 is removed by scraper blade 27. Following scraper blade 27, carpet structure 20 moves across lick roll 28. In the illustrated embodiment, carpet structure 20 is then monitored by the method of this invention to determine the distribution of the coating composition thereon. Following this monitoring, carpet structure 20 moves through a pair of marriage rolls 33 where a second backing layer 34, commonly referred to as secondary jute, is married to the coated carpet structure. From the marriage rolls 33, a heating zone (not shown) dries and/or cures the coating composition.

In the determination of the distribution of the coating composition 26 on carpet structure 20, light 40 emitted from light source 29 strikes an area of the coated surface of carpet structure 20 and at least a fraction of the light returned therefrom strikes detector 30, with the intensity of said fraction of light varying with the coating distribution on the carpet structure. Detector 30 provides a measurable signal which varies with the intensity of this light fraction. This signal is transmitted to recorder 31 by lead 19 and registered thereon. Analysis of said signal determines the distribution of coating composition 26 on carpet structure 20.

Alternatively, (or additionally), as depicted in the illustrated embodiment, detector 30 can be connected to a control unit; in which case the distribution of the coating composition 26 can be immediately and accurately controlled. Such control unit comprises a computing means 32 connected to detector 30 by means of lead 39 and to scraper blade 27, lick roll 28 and marriage rolls 33 by feedback leads 35, 36 and 37 and control leads 40, 41 and 42, respectively. In operation, the measurable signal provided by detector 30 is transmitted through lead 39 to computing means 32. Upon receipt of said signal, computing means 32 compares this provided signal, which relates to the distribution of coating composition 26 on carpet structure 20, to the desired distribution. Based on this comparison, computing means 32 adjusts process conditions, e.g., pressure of the scraper blade or marriage roll and speed or pressure of the lick roll, to give the desired coating distribution and properties to the carpet.

Although in the illustrated embodiment the coating distribution is determined following the lick roll, said distribution may be determined at any point following application of the coating to the carpet structure and prior to marriage of the secondary jute thereto. For example, the coating distribution is often advantageously determined immediately following the carpet's exposure to the scraper blade. Moreover, it is often advantageous to determine said distribution more than a single time in an operation, e.g., immediately following the carpet's exposure to the scraper blade and again following exposure to the lick roll, and to control the process conditions accordingly.

With regards to the various components useful in the practice of this invention, the light source of lamp is advantageously a source which emits a beam of light, preferably collimated light, at a constant intensity in a broad band of frequencies or selected narrow band. By "light" is meant electro-magnetic radiation of a suitable frequency, i.e., ultraviolet, visible or infrared. It may be a conventional incandescent source, such as a tungsten filament or a solid state light emitting source, such as a light emitting diode or a laser. Advantageously, the frequency of said light is in the visible or near infrared spectrum. Preferably, the frequency is such that the light returned to the detector is primarily due to the coating, with any light returned due to the uncoated surface being minimized. As such, the preferred frequencies are those which are absorbed by the uncoated surface, e.g., a blue light emitted onto a red carpet surface. Moreover, to reduce the influences of environmental light, the light source is advantageously of high intensity. For example, a conventional quartz-halogen filament light source of from about 100 to about 500 watts is beneficially employed.

In a normal operation, the light advantageously illuminates the back, i.e., coated side, of the carpet structure in a manner such that the intensity of the light returned therefrom relates to the distribution of the coating and maximizes any differences therein. For example, in coating a high gauge tufted carpet (a tufted carpet having a high number of yarn i.e., fiber bundles, per cm, e.g., greater than about two yarns per cm width), it is often desirable to completely coat the tufts to provide the carpet with the desired physical properties, e.g., maximum adhesion between the primary backing to the secondary jute (scrim adhesion). As such, the tuft tops and upper portion of at least one side of the tufts are advantageously illuminated, with illumination of that area between the tufts being deliberately avoided. In such applications, the angle of incidence is advantageously from about 2° to about 35°, preferably from about 5° to about 25°. Alternatively, for low gauge carpets, e.g., shag type carpets having a gauge of about one yarn per cm, wherein the majority of the coating composition available for adhesion of the primary backing to the secondary jute lies between the loops or tufts of the carpet yarns, the angle of incidence is advantageously some higher value, e.g., about 40° to about 85°. For other desired coating distributions, the angle of incidence most advantageously employed is easily determined by experimentation.

The intensity of a fraction of the returned light is measured by a detector means, which means converts the light which falls thereon into a measurable signal, e.g., an electrical current. This signal varies with the intensity of the light fraction. Light detectors conventionally employed as such, e.g., photometers and the like, are useful in the practice of this invention. Typically, such detectors consist of an electrical circuit containing a conductor element, the conductivity of which element varies in response to light. Advantageously, the detectors used in this invention are sensitive to very small quantities of light. Moreover, such detector beneficially has a very fast response due to the fact that the surfaces being illuminated are often moving at significant speeds. For example, in the application of a coating composition to a carpet backing, the carpet generally moves at speeds from about 15 to about 35 feet per minute. Furthermore, the "noise" generated by the detector, including any amplification of the signal generated thereby, should be a minimal amount. In operation, the detector will be subjected to some light not returned by the surface, i.e., environmental light. As such, the detector should be more sensitive to some light wave lengths than others. Hence, it is desirable to match the light source and detector. For example, a shielded IP28 photomultiplier sold by RCA coupled with a Keithley 602 electrometer sold by Keithley Instruments, Inc., has been found to be advantageously employed with a Bausch and Lomb microscope light source, Catalog No. 31-33-53 and other types of incandescent light. Other detectors, amplifiers and light sources can be readily selected by those in the art. To further minimize the effects of environmental light, the light source and detector may advantageously be housed within a housing member such that influences of environmental light are minimized.

The relative placement of the detector is not narrowly critical to the method of this invention, provided the light source and detector are maintained in a constant relative position throughout the operation, i.e., determination of the reference signal as hereinafter described and subsequent measurements using said reference signal. Such position is advantageously a position such that the maximum amount of returned light is collected by the detector.

In the normal practice of the method of this invention, the electrical or other signal produced by the detector, i.e., output signal, which may or may not be amplified, is advantageously recorded by some suitable recording means, e.g., recording chart or display screen.

The output signal provided by the detector relates to the distribution of the coating composition, i.e., (1) the amount of the illuminated surface which is coated and (2) the depth of such coating, on those surfaces which have been illuminated and analysis of the signal establishes the distribution of the coating on the carpet backing. Such analysis generally comprises (1) comparing the signal to a pre-established reference signal, advantageously, the signal generated by a sample of the uncoated carpet and (2) relating the differences thereof to the distribution of the coating composition on the carpet. Typically, an electrical circuit means connected to the detector (or alternatively the recorder) is employed for such purpose.

Alternatively, analysis of the coated carpet is accomplished by comparing said output signal to a pre-established reference signal (or range of such signals) established by conducting standard physical tests on a variety of carpet samples having coating distributions which generate different output signals. In such case, a carpet having desirable physical properties can be prepared without regard to the actual coating distribution. Moreover, by relating the intensity of light returned by a carpet sample having optimum physical properties to a known standard such as a known color or brightness standard, said distribution can easily be duplicated.

In a similar manner, the method of this invention is useful as a means for monitoring changes in the application process as manifested by the changes which occur in the distribution of the coating.

As used herein, the term "carpet structure" is intended to include those structures to which the coating composition is applied and which are employed in the preparation of a carpet as that term is conventionally employed. Representative carpets include tufted carpets; needle felt carpets; woven carpets; rugs including piled, woven and napped rugs; and the like. The term "coating composition" is intended to include any composition which is deposited on the carpet structure, provided that it has light deflecting properties sufficiently different from the materials which consititute the carpet structure being coated. By "sufficiently different light deflecting properties " is meant that the light deflecting properties of the carpet structure to be coated and the coating composition differ by an amount sufficient that a change in the coating distribution is measurable by the methods of this invention. Advantageously, said light deflecting properties differ by more than about 10 percent, preferably more than 20 percent when said difference is determined by comparing the intensity of light returned from each surface (separately) by the method of this invention.

To illustrate the practice of this invention, the following example is presented. The example should not be construed to limit the scope of this invention. All parts and percentages are by weight unless otherwise indicated.

EXAMPLE

A 'Y' search unit (for a Model 670 reflection meter sold by Photovolt Corporation) is placed directly above a tufted carpet section (low level loop) composed of red and black nylon yarns and a primary jute backing material (Sample No. 1). The carpet has an uncoated (greige) height of 0.63 cm and a gauge of about three yarns (fiber bundles) per cm of carpet width. A Photovolt ® Model 670 reflection meter is connected to the search unit in a manner such that it records the electrical signals provided therefrom. A constant intensity light source is placed about 35 cm from the center of the 'Y' search unit at an angle of incidence of about 13.6°.

The uncoated carpet is illuminated by the light source and the light returned from the illuminated surface falls upon the search unit. The electrical signal provided by the search unit, which is proportional to the intensity of light returned thereto, is indicated on the reflection meter and recorded.

A binder composition having the following formulation

| Ingredient | Dry Weight (g) | Wet Weight (g) |
|---|---|---|
| Latex (1) | 100 | 207.5 |
| CaCO$_3$ (2) | 400 | 400 |
| Polyacrylate Thickener (3) | 0.6 | 5 |
| Water | — | 64 |

(1) A carboxylated styrene-butadiene latex sold as DL 892 by The Dow Chemical Company
(2) Sold as #10 White by Georgia Marble
(3) Sold as Paragum ® 141 by Para-Chem, Inc.

is applied to the carpet backing such that a relatively uniform coating of the coating weight specified in Table I results. The coated carpet is then illuminated and the signal provided by the search unit, said signal varying with the intensity of light returned from the illuminated surface, is registered by the reflection meter.

In a similar manner, similar uncoated carpet sections (Samples Nos. 2–9) are illuminated and the signal provided by the search unit registered by the reflection meter. Each of these carpet samples are then coated with an identical binder composition at various coating weights, as specified in Table I, to a relatively uniform coating. Each of the coated sections are illuminated and the reading provided by the search meter recorded.

A secondary jute layer is married to each of the coated carpet sections by means of a weighted roller. These sections are then placed on an open mesh frame and placed in a hot air oven at 135° C. for about 15 minutes. At the end of this period, they are removed from the oven and conditioned for 24 hours at 22° C. and 50 percent relative humidity. Each carpet section is then tested for scrim adhesion.

The results of the scrim adhesion testing, the readings of the reflection meter for the coated and uncoated carpet samples and the coat weight for each carpet sample are recorded in the accompanying table.

TABLE I

| Sample No. | Reading, Uncoated Carpet (1) | Reading, Coated Carpet (2) | Δ Reading (3) | Coating Weight gm/m$^2$ (4) | Scrim Adhesion kg/cm (5) |
|---|---|---|---|---|---|
| 1 | 46.5 | 70 | 23.5 | 1070 | 0.53 |
| 2 | 46.7 | 72 | 25.3 | 1000 | 0.49 |
| 3 | 46.3 | 72 | 25.7 | 970 | 0.57 |
| 4 | 46.5 | 75 | 28.5 | 1220 | 0.57 |
| 5 | 47.5 | 78 | 30.5 | 1190 | 0.75 |
| 6 | 46.1 | 78 | 31.9 | 920 | 0.79 |
| 7 | 46.5 | 81 | 34.5 | 1190 | 0.75 |
| 8 | 47.4 | 84 | 36.6 | 1150 | 0.94 |
| 9 | 46.2 | 84.5 | 38.3 | 1130 | 1.0 |

(1) Reading refers to the reading of the reflection meter upon illumination of the uncoated carpet section following calibration of the reflection meter.
(2) Same as (1) except the reading is that of the coated carpet.
(3) Δ Reading is the difference between the reading of the reflection meter for the coated carpet and uncoated carpet, with the higher Δ reading indicating a greater amount of surface area being coated and/or a greater depth of said coating.
(4) Coating weight is the weight in grams of latex deposited on a square meter of the carpet material. It is determined by first weighing the uncoated predried carpet having a known surface area. The carpet is then coated and the latex applied thereon dried and cured. The carpet and cured latex are then immediately weighed. The coating weight is then determined by the following equation:

$$\frac{(W_c - W_u)}{S_B}$$

wherein $W_u$ is the weight of the uncoated carpet, $W_c$ is the weight of the coated carpet and $S_B$ is the surface area of the carpet backing in square meters.
(5) Scrim adhesion is determined by pulling a 7.6 cm wide section of the secondary jute from the remainder of the carpet backing on an Instron$^R$ tester at a speed of 30.5 cm per minute. The scrim adhesion value recorded is the total force required to pull the secondary jute from the backing per one cm width of the jute.

As evidenced by the data recorded in the accompanying table, the method of this invention accurately predicts the scrim adhesion of the various coated carpet samples. The coating weight, i.e., the quantity of the coating composition on the carpet backing, does not predict with accuracy the scrim adhesion.

What is claimed is:

1. A method for determining the distribution of a coating composition on a carpet structure, wherein the coating composition and the carpet structure being coated have sufficiently different light deflecting properties, said method comprising:
   (a) illuminating a surface of the carpet structure, at least a portion of said surface having the coating composition deposited thereon, and
   (b) measuring the intensity of at least a fraction of the light returned therefrom, the intensity of said light fraction varying with the distribution of the coating composition on the carpet structure.

2. The method of claim 1 wherein the carpet structure is a tufted, woven or needle felt carpet.

3. The method of claim 1 wherein the returned light strikes a light detector which provides a measurable signal which varies with the intensity of the returned light.

4. The method of claim 3 wherein the measurable signal provided by the detector is registered on a recorder means.

5. The method of claim 3 which further comprises enclosing the light source and detector within a housing which reduces the influence of environmental light.

6. The method of claim 1 wherein two light sources are employed to illuminate the surface of the carpet structure.

7. The method of claim 6 wherein the two light sources are at the same angle of incidence and positioned diametrically opposite one another.

8. The method of claim 1 wherein three or more light sources are employed to illuminate the carpet structure, each light source having the same angle of incidence and being essentially equidistant from both light sources adjacent thereto.

9. In a method for coating a carpet structure of the type including the steps of:
  (a) applying a coating composition to the carpet structure,
  (b) removing any excess composition which may have been applied, and
  (c) marrying a second backing layer to the coated carpet structure;
the improvement which comprises
  (d) determining the distribution of the coating composition at some point between steps (b) and (c) by the method of claim 1.

10. The method of claim 9 further comprising the step of controlling the distribution of the coating composition on the carpet structure.

11. In a method for coating a carpet structure of the type including the steps of:
  (a) passing the back side of the carpet structure across an applicator roll rotating in a reservoir of the coating composition to transfer the coating composition from the roll to the carpet structure,
  (b) passing the back side of the coated carpet structure over a scraper blade to remove any excess coating composition, and
  (c) passing the coated carpet structure and a second backing material through marriage rolls to marry the second backing material to the coated carpet structure;
the improvement which comprises
  (d) determining the distribution of the coating at some point between steps (b) and (c) by the method of claim 1.

12. The method of claim 11 further comprising the step of controlling the distribution of the coating composition by adjusting the pressure of the scraper blade or marriage rolls.

13. The method of claim 11 further comprising the step of passing the carpet structure across a lick roll at some point between steps (b) and (c).

14. The method of claim 13 further comprising the step of controlling the distribution of the coating composition on the carpet structure by adjusting the pressure of the scraper blade or marriage rolls or adjusting the speed of the lick roll.

* * * * *